US006251932B1

(12) United States Patent
Reichelt et al.

(10) Patent No.: US 6,251,932 B1
(45) Date of Patent: Jun. 26, 2001

(54) IMMUNOPHILIN LIGANDS

(75) Inventors: Dietmar Reichelt, Eschau; Berhard Kutscher, Maintal; István Szelényi, Schwaig; Hildegard Poppe, Dresden; Gerhard Quinkert, Glashütten; Kay Brune, Marloffstein; Holger Bang, Erlangen; Holger Deppe, Frankfurt, all of (DE)

(73) Assignee: ASTA Medica AG (DE)

( * ) Notice: Subject to any disclaimer, the term of this patent is extended or adjusted under 35 U.S.C. 154(b) by 0 days.

(21) Appl. No.: 09/161,037

(22) Filed: Sep. 25, 1998

(51) Int. Cl.$^7$ .................. C07D 401/06; A61K 31/405
(52) U.S. Cl. ........................ 514/414; 548/455
(58) Field of Search ................ 548/455; 514/414

(56) References Cited

FOREIGN PATENT DOCUMENTS

| 19542189 A1 | 5/1997 | (DE) . |
| 19616509 A1 | 1/1998 | (DE) . |
| 769498 A1 | 4/1997 | (EP) . |
| 04154732 | * 10/1990 | (JP) .................. 548/183 |

OTHER PUBLICATIONS

Quinkert et al.: Variation and Selection, Helv. Chim. Acta 79, (1966), pp. 1260–1278.
P.D. Croce et al.: 2–(Tozylaminobenzyl)trimethylammonium halides as precursors of 2–substituted indoles, CA 126, 1997 117836p.

H. Ishikawa et al.: Preparation of (pyrrolidinylcarboxamido)benzene derivatives of intermediates for antibacterial pyrroloquinones, CA 120, 1994, 106753j.

S. Torii et al.: A process for the preparation of N–sulfonylindoline derivatives as intermediates for pharmaceuticals and agrochemicals, CA 109, 1988, 92779f.

C.B. Hudson et al.: The synthesis and chemistry of DL–indoline–2–carboxylic acid , CA 68, 1968, 21773y.

* cited by examiner

*Primary Examiner*—Robert Gerstl
(74) *Attorney, Agent, or Firm*—Gabriel P. Katona LLP

(57) ABSTRACT

The invention relates to an immunophilin ligand of Formula I and having antiasthmatic, antiallergic, antirheumatic, immunosuppressant, antipsoriatic and neuroprotectant properties, (I)

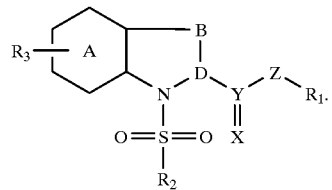

19 Claims, No Drawings

IMMUNOPHILIN LIGANDS

FIELD OF THE INVENTION

The invention relates to novel specific immunophilin ligands with antiasthmatic, antiallergic, antirheumatic, immunosuppressant, antipsoriatic and neuroprotectant properties.

BACKGROUND

Cyclosporin A (CsA) and FK 506 are immunosuppressant natural substances derived from fungi which inhibit the $Ca^{2+}$-dependent signal transmission pathway in some cell types. In T cells, both agents inhibit the transcription of a number of genes, including the gene for IL-2, which is activated by stimulation of the T cell receptors (TCR). FK 506 and CsA both bind with high affinity to soluble receptor proteins (G. Fischer et al., Nature 337, 476–478, 1989, M. W. Harding et al., Nature 341, 755–760, 1989). The FK 506 receptor was called FKBP, the CsA receptor cyclophilin (Cyp). Both proteins catalyse the isomerization of cis- and trans-amide bond rotamers of peptides and are also frequently called immunophilins.

The supramolecule of CsA-Cyp or FK 506-FKBP binds calcineurin (CN) and inhibits its phosphatase activity. A cellular target molecule of CN was recognized as the cytosolic, phosphorylated component of the transcription factor NF-AT which, with inadequate CN activity for the action in the cell nucleus, cannot be dephosphorylated and thus the active transcription complex on the IL-2 promoter cannot be switched on (M. K. Rosen, S. L. Schreiber, *Angew. Chem* 104 (1992); 413–430; G. Fischer, *Angew. Chem.* 106 (1994), 1479–1501).

The allergic, asthmatic disorders are based on an inflammatory reaction which is controlled by T cells and their mediators. Corticosteroids are still the agent of choice in the treatment of many allergic disorders. CsA and FK 506 also proved in animal experiments and in clinical studies to be a favorable therapeutic in bronchial asthma and underlying inflammations. In animal experiments, it was possible to show the blockade of various cytokines such as IL-2, IL-4 and IL-5, which cause allergically induced inflammations. Despite the multiplicity of attempts at the identification of novel active immunophilin inhibitors, it was not possible until now to prepare or isolate any more efficacious structures than CsA, FK 506, rapamycin or derivatives of these natural substances. The high inhibitory potential of CsA, FK 506 or rapamycin, however, is very considerably reduced by the manifold side effects, in particular of the kidneys, and neurotoxicity (N. H. Sigal et al., *J. Exp. Med.* 173, 619–628, 1991). What lies behind this fact is the non-specificity of the interaction between immunophilin ligands and the cell-specific binding proteins. As a result, the known medicinal therapeutic action of these immunosuppressants is considerably restricted. Furthermore, the inadequate selectivity of the compounds proves problematical, particularly in long-term therapy.

A further compound having immunosuppressant properties was discovered during the screening of substance mixtures (G. Quinkert, H. Bang and D. Reichert, *Helv. Chim. Acta* 1996, 79, 1260). The structure published there is an indoline-2-carboxamide which at 10 μmol exhibited an inhibition of IL-2 proliferation of 77% and at 1 μmol an inhibition of IL-2 proliferation of 12%. New measurements at a concentration of 10 μmol showed an IL-2-dependent inhibition of proliferation of 29%.

A substance class which likewise contains indolinecarboxylic acid as a central unit and exhibits immunosuppressant properties as well as antiasthmatic properties was described in German patent No. 1,961,6509.1.

DESCRIPTION OF THE INVENTION

It is an object of the present invention is to provide novel immunophilic ligands having useful pharmacological properties and providing processes for their targeted synthesis.

It has been found that the novel immunophilin ligand of Formula I surprisingly satisfies the aforementioned object of the present invention. The compounds of Formula I are

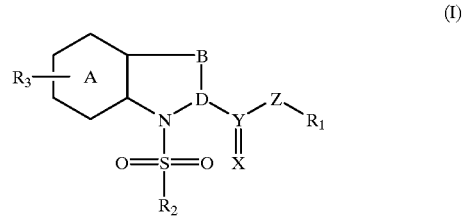

(I)

wherein $R_1$, $R_2$ and $R_5$ are independently of each other hydrogen, $C_{1-12}$ alkyl or $C_{2-6}$ alkoxy groups in which the alkyl group is straight-chain or branched and can be substituted with a mono- or bicyclic heteroaryl group having 1–4 heteroatoms suitably independently of each other N, S, and O, or mono- or polysubstituted with a phenyl ring, or $R_1$ is an amine group of an amino acid methyl ester from the group of histidine, leucine, valine, serine, threonine, pipecolic acid, 4-piperidine-carboxylic acid, 3-piperidinecarboxylic acid, —$NH_2$-lysine, —Z-NH-lysine, -(21-Z)-NH-lysine, 2-pyridylalanine, phenylalanine, tryptophan, glutamic acid, arginine, asparagine, citrulline, homocitrulline, ornithine, thiazole-carboxylic acid, proline, 2-indolinecarboxylic acid, octahydroindolinecarboxylic acid, tetrahydroisoquinolinecarboxylic acid, 5-aminovaleric acid, and 8-aminooctanoic acid; and $R_2$ is an amino $C_{1-12}$ alkyl, or an amino $C_{2-6}$ alkoxy group wherein the alkyl group is straight-chain or branched and can be substituted with a mono- or bicyclic heteroaryl group having 1–4 heteroatoms suitably independently of each other N, S, and O, or mono- or polysubstituted with a phenyl ring, $R_3$ is H, F, $OR_4$, Br, $NHR_4$ $R_4$ is hydrogen, a $C_{3-7}$ cycloalkyl, $C_{1-6}$ alkyl, or carboxy $C_{1-6}$ alkyl group wherein the alkyl group is straight-chain or branched, A is without a ring, or an aromatic, non-aromatic, or aromatic heterocyclic or non-aromatic heterocyclic having 1–2 heteroatoms, suitably independently of each other N, S and O, B is CH D is CH B—D is CH=C X is O, S, H Y is S, C, and when X is=$H_2$ then a single bond; and Z is S, O, $NR_5$.

At least in one of $R_1$, $R_2$ and $R_5$ independently of each other the alkyl group in said alkoxy group, and in $R_2$ in said amino $C_{2-6}$ alkoxy group, is substituted with a morpholine, piperazine, piperidine, pyridine, isoquinoline, quinoline, pyrimidine, oxazole, oxadiazole, isoxazole, pyrazole, pyrrole, indole, indazole, phthalazine, thiophene, furan or imidazole group.

Either of said phenyl rings in at least one of $R_1$, $R_2$ and $R_5$ can be independently of each other mono- or polysubstituted with the substituent halogen, $C_{1-6}$ alkyl, $C_{3-7}$ cycloalkyl, carbamoyl, trifluoromethyl, hydroxyl, methoxy, ethoxy, benzyloxy, amino, carboxyl, or carboxyl residue esterified with a straight chain or branched $C_{1-6}$ alkanol. In at least one of $R_1$, $R_2$ and $R_5$ independently of each other the aforementioned substituent is suitably substituted with one or more of a benzyl, benzoyl, acetyl group.

In $R_2$ the aforesaid substituent can also be substituted with a mono-, bi- or tricyclic aminoaryl or aminoheteroaryl group having 1–4 heteroatoms suitably independently of each other N, S, and O, or by a carboxy $C_{1-12}$ alky, carboxycyclopentyl, carboxycyclohexyl or benzoyl group which can be mono- or polysubstituted by a halogen, methoxy, amino, carbamoyl, trifluoromethyl, carboxyl residue, or with a carboxyl group esterified with straight-chain or branched $C_{1-6}$ alkanol.

In $R_4$ the alkyl group in the carboxy $C_{1-6}$ alkyl group can be substituted with a mono-, bi- or tricyclic carbonylaryl or carbonylheteroaryl residue having 1–4 heteroatoms suitably independently of each other N, S and O.

In $R_2$ the aryl or heteroaryl group can be mono- or polysubstituted with the substituent halogen, $C_{1-6}$ alkyl, $C_{3-7}$ cycloalkyl carbamoyl, trifluoromethyl, hydroxyl, methoxy, ethoxy, benzyloxy, amino, carboxyl, or carboxyl group esterified with a straight chain or branched $C_{1-6}$ alkanol, and the aforementioned substituent can also be substituted with one or more of a benzyl, benzoyl, acetyl group.

The invention furthermore relates to the pharmaceutically acceptable salts of the compounds of Formula I, the processes for the preparation of the compounds of Formula I, and processes for their pharmacological use.

This class of compounds and their pharmaceutically acceptable salts have a high affinity for immunophilins such as CypA, CypB, CypC and FKBP12. Moreover, substances of Formula I inhibit various cytokine syntheses, as well as a $Ca^{++}$-dependent signal transmission pathway.

Those compounds of Formula I which contain asymmetric carbon atoms and therefore as a rule occur as racemates can be separated into the optically active isomers in a manner known per se, for example using an optically active acid. However, the possibility also exists of employing optically active starting substances to begin with, corresponding optically active or diastereoisomeric compounds then being obtained as the final product. The invention thus comprises compounds of Formula I which contain an asymmetric carbon atom, the R form, the S form and R, S mixtures, and, the case of a number of asymmetric carbon atoms, the diastereoisomeric forms.

The compounds of the present invention stand out markedly at the C terminus and in their optical purity of the indolinecarboxylic acid from the indoline-2-carboxylic structure referred to in the aforementioned publication of Quinkert, et al., and additionally show a markedly better antiasthmatic, antiallergic, antirheumatic, antiinflammatory, antipsoriatic and immunosuppressant activity. The indolinecarboxylic acid substances described in the aforementioned German patent No. 1,961,6509.1 differ significantly at the N terminus from the substances of the present invention.

Depending on the process conditions and starting substances, the compounds of Formula I can be obtained as free compounds or in the form of their salts. The salts obtained can be converted into the free bases or acids in a manner known per se, for example by using acids, alkali or ion exchangers.

The compounds of Formula I liberated in this manner can be converted into the corresponding pharmaceutically acceptable acid addition salts using inorganic or organic acids or bases, such as hydrochloric acid, hydrobromic acid, phosphoric acid, sulfuric acid, acetic acid, tartaric acid, citric acid, fumaric acid, maleic acid, lactic acid or embonic acid, or with an inorganic or organic base.

Both the free bases and their salts are biologically active. The compounds of Formula I can be administered in free form or as a salt with a pharmaceutically acceptable acid or base. Administration can be carried out orally, parenterally, intravenously, transdermally or by inhalation. The present invention further relates to pharmaceutical preparations which contain at least one compound of Formula I or its salts with pharmaceutically acceptable inorganic or organic acids or bases and, if appropriate, pharmaceutically acceptable excipients and auxiliaries.

Suitable forms of administration forms include tablets or coated tablets, capsules, solutions or ampoules, suppositories, patches or inhalable powder preparations.

The dose of the aforementioned dosage forms depends on the condition of the patient and on the dosage form itself. The daily dose of active compound is suitably between about 0.01 and about 100 mg per kg of body weight per day. More suitable dosages can be determined by routine dosage ranging.

According to the present invention, the compounds of Formula I can be prepared by the following alternative processes.

1$^{st}$ process:

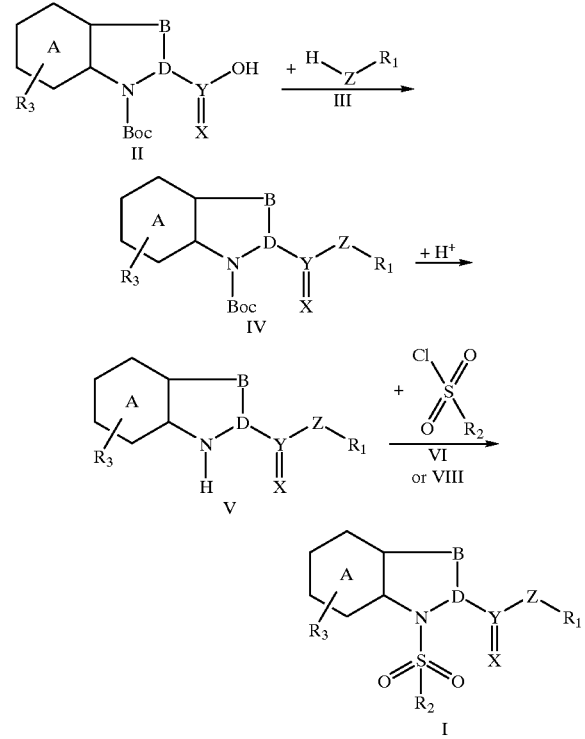

In the first process shown above, the compounds of Formula I of the present invention are prepared by reacting a carboxylic acid derivative of Formula II with an amine, alkanol, halogen compound or tosylate (H—Z—R.) of Formula III to provide amide, ester or ether of Formula IV, then reacting this derivative of Formula IV, after deprotection with acid, to give an intermediate of Formula V, and in a continuing reaction reacting with a compound of Formula VI, or with a compound of Formula VIII (see 2$^{nd}$ process), provide the target compound of Formula I. In all of these and in the subsequently shown formulae the substituent definitions are the same as provided for the same symbol in connection with the description of Formula I.

2$^{nd}$ process:

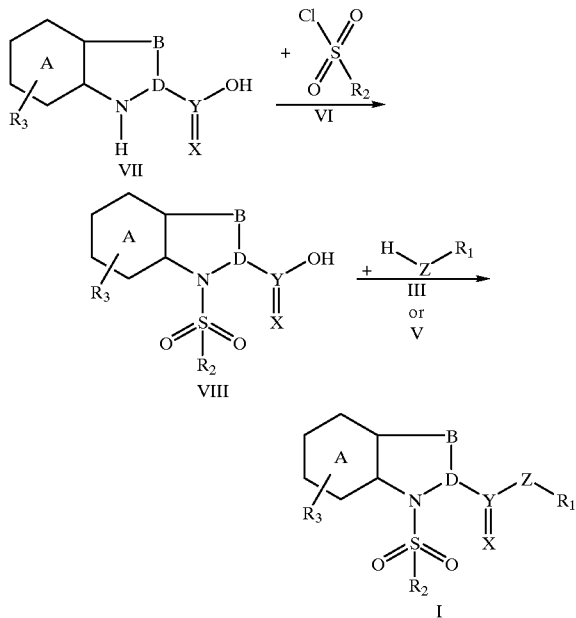

In the second process, the compounds of Formula I of the present invention are prepared by reacting a carboxylic acid derivative of Formula VII with a sulfonyl chloride of Formula VI, and in a continuing reaction reacting with a compound of Formula III, or with a compound V, to provide the target compound of Formula I.

The compounds of Formula I of the present invention are distinguished by immunophilin binding and inhibit isomerase activity. This prolyl isomerase activity is tested according to a conventional, well known enzyme test described in G. Fischer, H. Bang. Mech, *Biomed. Biochim. Acta,* 43, 1101–1111; G. Fischer, H. Bang, A Schellenberger, *Biochim. Biophys. Acta,* 791, 87–97, 1984; D. H. Rich et al., *J. Med. Chem.* 38, 4164–4170, 1995.

Without the peptidyl cis-trans isomerase activity of the immunophilins being affected in each case, such compounds surprisingly specifically inhibit the TNF-α, GM-CSF, IL-2, IL-4 and IL-5 proliferation of mast cells, macrophages and activated T cells. The compounds of the present invention can be employed, like cyclosporin A (Sandimmun ®, CsA), FK 506 or rapamycin (Tacrolimus) as immunosuppressants (R. Y. Caine et al., *Br. Med. J.* 282, 934–936, 1981), for the treatment of autoimmune disorders (R. H. Wiener et al., *Hepatology* 7, 1025, Abst. 9, 1987; L. Fry, *J. Autoimmun.* 5, 231–240, 1992, G. J. Feutren, *J. Autoimmun.* 5, 183–195, 1992, EP 610,743), allergic inflammations (P. Zabel et al., *Lancet* 343, 1984), as antiasthmatics (C. Bachert, Atemw.-Lungenkrkh. 20, 59, 1994), for insulin-dependent diabetes mellitus (C. R. Stiller, *Science,* 223, 1362–1367, 1984), sepsis, as a neuroprotectant or for neuroregeneration in multiple sclerosis, Alzheimer s and Parkinson s disease (U.S. Pat. No. 5,614,547, JP 08 333 334, *Nature Medicine,* 3, 4, 1997), antirheumatics, psoriasis (SANDORMA, 4, 1995) and also in combination with known immunophilin ligands such as CsA, FK 506 or rapamycin (M. J. Wyvratt, N. H. Sigal, *Perspectives in Drug Discovery and Design, Immunosuppression,* 2, 1, 1994; WO 92/21313, U.S. Pat. No. 5,330,993).

The invention is illustrated in greater detail below with reference to further examples, using the following abbreviations:

AcOEt ethyl acetate
Boc tert-butyloxycarbonyl
(Boc)$_2$O tert-butyric anhydride
CN calcineurin
CsA cyclosporin A
Cyp cyclophilin
DMAP N,N-dimethylaminopyridine
EA elementary analysis
FKBP FK 506 binding protein
HPLC high-pressure liquid chromatography in OPV in an oil pump vacuum
soln solution
MeOH methanol
PPlase peptidyl-proline cis-trans isomerase in RE in a rotary evaporator in vac. under vacuum
RT room temperature
rac racemic
ent enantio
TFA trifluoroacetic acid
Z benzyloxycarbonyl General procedure for the preparation of carboxamides of Formula IV 1 eq. (3.3 mmol) of the Boc-protected carboxylic acid, 1 eq. (3.3 mmol) of the appropriate amine and 1.5 eq. (4.9 mmol) of 2-chloro-1-methyl-pyridinium iodide and 2.5 eq. (8.1 mmol, 1.13 ml) of triethylamine (TEA) were dissolved or suspended together in dichloromethane (DCM), and the mixture was stirred for 30 min and refluxed for 6 hours. The solvent was distilled off on a rotary evaporator and the residue was taken up in AcOEt. This suspension was washed twice each with aqueous KHSO$_4$ solution, with aqueous NaOH solution and once with aqueous, saturated NaCl solution, dried over Na$_2$SO$_4$ and purified by chromatography on silica gel using AcOEt/hexane or using a CH$_2$Cl$_2$/MeOH mixture.

General procedure for the preparation of sulfonamides of Formula VIII 100 mmol of the amino acid were suspended in water and treated with 300 mmol of NaOH and with 110 mmol of sulfonyl chloride and the mixture was heated at 90° C. for 4 hours. After cooling, it was acidified with aqueous 2N HCl, and the precipitated product was filtered off with suction and dried at 40° C.

General procedure for the preparation of compounds of Formula I 4.7 mmol of Boc-protected carboxamide of Formula IV were stirred at room temperature for 2 hours in DCM/TFA 4:1. The solvent and excess TFA were removed in vac. The oily residue was stirred at 35° C. for 24 hours in 120 ml of DCM with a sulfonamide (7 mmol) of Formula VI, with 11.7 mmol of TEA and 7.7 mmol of Mukaiyama reagent. The solvent was distilled off on a rotary evaporator and the residue was taken up in AcOEt. This suspension was washed twice each with aqueous KHSO$_4$ solution, with aqueous NaOH solution and once with saturated aqueous NaCl solution, then dried over Na$_2$SO$_4$ and purified by chromatography on silicagel using AcOEt/hexane or using a CH$_2$Cl$_2$/MeOH mixture.

The following compounds of Formula I were prepared according to these general procedures:

EXAMPLE 1

(2S)-1-[((2S)-1-(4-acetylamino)phenylsulfonyl)indolin-2-yl)carbon-yl]-N-(2-methoxyethyl)indoline-2-carbamide M.p.: 224–227° (dec.) (AcOEt/PE).

TL: DM/MeOH 95:5; R$_f$ 0.35.

$^1$H NMR (270 MHz, (D$_6$) DMSO): 2.01 (s, 3H); 3.08 (s, 3H); 3.09–3.83 (m, 8H); 4.70–5.45 (m, 2H); 6.93–7.41 (m, 7H); 7.62–8.16 (m, 5H); 8.45–8.73 (m, 1H); 10.44 (s, 1H).

EA: cal. for $_{29}$H$_{30}$N$_4$O$_6$S 61.91 H 5.37 N 9.96; found: 60.42 H 5.15 N 9.64.

EXAMPLE 2

(2R)-1-[((2S)-1-(4-acetylamino)phenylsulfonyl)indolin-2-yl)-carbonyl]-N-(2-methoxyethyl)indoline-2-carbamide M.p.: 223–227° (dec.) (AcOEt/PE).

TL: DM/MeOH 95:5; R$_f$ 0.35.

$^1$H NMR (270 MHz, (D$_6$) DMSO): 2.0 (s, 3H); 3.09 (s, 3H); 3.10–3.70 (m, 8H); 4.77–5.51 (m, 2H); 6.89–7.39 (m, 7H); 7.60–8.21 (m, 5H); 8.31–8.59 (m, 1H); 10.39 (s, 1H).

MS (ESI$^+$): cal. for $_{29}$H$_{30}$N$_4$O$_6$S, M=562.65; found: M$^+$563.72.

EXAMPLE 3

(2S)-1-[((2R)-1-(4-acetylamino)phenylsulfonyl)indolin-2-yl)-carbonyl]-N-(2-methoxyethyl)indoline-2-carbamide M.p.: 224–227° (dec.) (AcOEt/PE).

TL: DM/MeOH 95:5; R$_f$ 0.35.

$^1$H NMR (270 MHz, (D$_6$) DMSO): 2.02 (s, 3H); 3.00 (s, 3H); 3.15–3.80 (m, 8H); 4.72–5.40 (m, 2H); 6.98–7.44 (m, 7H); 7.66–8.22 (m, 5H); 8.48–8.70 (m, 1H); 10.52 (s, 1H).

MS (ESI$^+$): cal. for $_{29}$H$_{30}$N$_4$O$_6$S, M=562.65; found: M$^+$=563.71.

EXAMPLE 4

(2R)-1-[((2R)-1-(4-acetylamino)phenylsulfonyl)indolin-2-yl)-carbonyl]-N-(2-methoxyethyl)indoline-2-carbamide M.p.: 221–225° (dec.) (AcOEt/PE).

TL: DM/MeOH 95:5; R$_f$ 0.35.

$^1$H NMR (270 MHz, (D$_6$) DMSO): 2.08 (s, 3H); 3.00 (s, 3H); 3.11–3.76 (m, 8H); 4.72–5.39 (m, 2H); 6.88–7.47 (m, 7H); 7.62–8.17 (m, 5H); 8.41–8.68 (m, 1H); 10.43 (s, 1H).

MS (ESI$^+$): cal. for $_{29}$H$_{30}$N$_4$O$_6$SM=562.65 found: M$^+$=563.7.

EXAMPLE 5

(2R,S)-1-[((2R,S)-1-(4-acetylaminophenylsulfonyl)indolin-2-yl)-carbonyl]-N-(2-methoxyethyl)indoline-2-carbamide M.p.: 220–225° (dec.) (AcOEt/PE).

TL: DM/MeOH 95:5; R$_f$ 0.35.

$^1$H NMR (270 MHz, (D$_6$) DMSO): 2.05 (s, 3H); 3.10 (s, 3H); 3.06–3.75 (m, 8H); 4.72–5.40 (m, 2H); 6.91–7.41 (m, 7H); 7.68–8.26 (m, 5H); 8.46–8.79 (m, 1H); 10.41 (s, 1H).

EA: cal. for $_{29}$H$_{30}$N$_4$O$_6$S x ¼ H$_2$O (567.15) 61.41 H 5.42 N 9.87; found: 61.23 H 5.51 N 9.63.

EXAMPLE 6

(2S)-1-[((2S)-1-(4-aminophenylsulfonyl)indolin-2-yl)carbonyl]-N-(2-methoxyethyl)indoline-2-carbamide TL: DM/MeOH 95:5; R$_f$ 0.16.

$^1$H NMR (270 MHz, (D$_6$) DMSO): 2.0 (s, 3H); 3.02–3.8 (m, 8H); 4.72–5.35 (m, 2H); 6.15 (s, NH$_2$); 6.91–7.41 (m, 7H); 7.68–8.26 (m, 5H); 8.3–8.7 (m, 1H).

EXAMPLE 7

($^2$S)-1-[((2S)-1-(4-aminophenylsulfonyl)prolyl)carbonyl]-N-(2-methoxyethyl)indoline-2-carbamide TL: DM/MeOH 95:5; R$_f$ 0.12.

$^1$H NMR (270 MHz, (D$_6$) DMSO): 1.7 (m, 2H); 1.9 (m, 2H); 2.05 (s, 3H); 3.0–3.74 (m, 6H); 4.5 (m, 1H); 5.1 (m, 1H); 6.05 (s, NH$_2$); 7.0–7.65 (m, 7H); 8.2 (m, 1H).

EXAMPLE 8

(2S)-1-[((2S)-1-(4-aminophenylsulfonyl)-4-piperidinyl)carbonyl]-N-(2-methoxyethyl)indoline-2-carbamide TL: DM/MeOH 95:5; R$_f$ 0.14.

$^1$H NMR (270 MHz, (D$_6$) DMSO): 1.55 (m, 2H); 1.85 (m, 2H); 2.03 (s, 3H); 2.3–2.4 (m, 2H); 2.85–3.65 (m, 6H); 4.1 (m, 1H); 5.15 (m, 1H); 6.05 (s, NH2); 7.0–7.65 (m, 8H); 8.4 (m, 1H).

EXAMPLE 9

[(2S)-1-acetyaminophenylsulfonyl)-4-piperidinyl)carbonyl]-N-(2-methoxyethyl)indoline-2-carbamide TL: DM/MeOH 95:5; R$_f$ 0.42.

$^1$H NMR (270 MHz, (D$_6$) DMSO): 1.7 (m, 2H); 1.9 (m, 2H); 2.05 (s, 3H); 3.0–3.74 (m, 6H); 4.54 (m, 1H); 5.1 (m, 1H); 7.0–7.75 (m, 8H); 8.25 (m, 1H).

EXAMPLE 10

(2S)-1-[(8-quinolinylsulfonyl)]-N-(2-methoxyethyl)indolinecarbamide

TL: DM/MeOH 95:5; R$_f$ 0.46.

$^1$H NMR (270 MHz, (D$_6$) DMSO): 3.08 (s, 3H); 3.09–3.83 (m, 4H); 6.15 (m, 1H); 6.65–8.65 (m, 10H); 9.15 (s, 1H).

EXAMPLE 11

1-[(2S)-1-(4-acetylaminophenylsulfonyl)indolin-2-yl)carbonyl]-N-leucine

MS (ESI$^+$): cal. for $_{23}$H$_{27}$N$_4$O$_5$S, M=471.56; found: M$^+$=471.9, M$^+$+Na$^+$=495.3

EXAMPLE 12

(S)-N-{(2S)-1-[4-(acetylamino)phenylsulfonyl]indolin-2-yl}carbonyl-N-(benzyloxycarbonyl)lysine methyl ester M.p.: 189–192° (AcOEt/PE).

TL: DM/MeOH 95:5; R$_f$ 0.3.

¹H NMR (270 MHz, DMSO): 1.2–1.45 (m, 4H); 1.6–1.76 (m, 2H); 2.08 (s, 3H); 2.78–3.21 (m, 5H); 3.63 (s, 3H); 4.25 (m, 1H); 4.8–4.92 (m, 1H); 5.02 (s, 2H); 6.93–7.45 (m, 9H); 7.65–7.75 (m, 4H); 8.40 (m, 1H); 10.33 (s, 1H)

EA: cal. for $_{32}H_{36}N_4O_8S$ (636.83) 60.36 H 5.70 N 8.8; found: 60.27 H 5.93 N 8.92.

EXAMPLE 13

Methyl (E)-({(2S)-1-[4(acetylamino)phenylsulfonyl] indoln-2-yl}-carbonyl)-4-(aminophenyl)acrylate M.p.: 167–171° (AcOEt)

TL: DM/MeOH 95:5; $R_f$ 0.63.

¹H NMR (270 MHz, DMSO): 2.11 (s, 3H); 3.05–3.11 (m, 1H); 3.27–3.36 (m, 1H); 3.71 (s, 3H); 4.95 (dd, $J_1$=4.1, $J_2$=13, 1H); 6.68 (d, J=16.1, 1H); 7.00–7.83 (m, 12H); 10.37 (s, 1H); 10.48 (s, 1H).

EA: cal. for $_{27}H_{25}N_3O_6S$ x ⅛ H₂O (521.83): 62.14 H 4.87 N 8.01; found: 62.28 H 5.10 N 7.72.

EXAMPLE 14

(2S)-1-[((2S)-1-(1-naphthalenylsulfonyl)indolin-2-yl)carbonyl]-N-(2-methoxyethyl)indoline-2-carbamide TL: DM/MeOH 95:5; $R_f$ 0.35.

¹H NMR (270 MHz, (D₆) DMSO): 2.05 (s, 3H); 3.10 (s, 3H); 3.0–3.7 (m, 8H); 4.8–5.2 (m, 2H); 6.93–7.41 (m, 7H); 7.7–8.4 (m, 9H).

EXAMPLE 15

(2S)-1-[((2S)-1-(2-Naphthalenylsulfonyl)indolin-2-yl)carbonyl]-N-(2-methoxyethyl)indoline-2-carbamide M.p.: 224–227° (dec.) (AcOEt/PE).

TL: DM/MeOH 95:5; $R_f$ 0.35.

¹H NMR (270 MHz, (D₆) DMSO): 2.0 (s, 3H); 3.06 (s, 3H); 3.1–3.8 (m, 8H); 4.75–5.5 (m, 2H); 6.93–7.41 (m, 7H); 7.7–8.4 (m, 9H).

EXAMPLE 16

(2S)-1-[((2S)-1-(4-methylphenylsulfonyl)indolin-2-yl)carbonyl]-N³-(N-propylimidazole)indoline-2-carbamide TL: DM/MeOH 95:5; $R_f$ 0.26.

¹H NMR (270 MHz, (D₆) DMSO): 1.95 (m, 2H); 2.3 (s, 3H); 3.1 (m, 2H); 4.05 (m, 2H); 4.64 (m, 1H); 5.1 (m, 1H); 6.9–7.85 (m, 15H); 8.2 (m, 1H).

EXAMPLE 17

(2S)-1-[((2S)-1-(4-methylphenylsulfonyl)indolin-2-yl)carbonyl]-N²-(N-ethylmorpholine)indoline-2-carbamide TL: DM/MeOH 95:5; $R_f$ 0.24.

¹H NMR (270 MHz, (D₆) DMSO): 1.5–1.7 (m, 4H); 1.9 (m, 4H); 2.25 (s, 3H); 2.75 (m, 2H); 3.65 (m, 2H); 4.72–5.35 (m, 2H); 6.91–7.71 (m, 12H); 8.4 (m, 1H).

EXAMPLE 18

(2S)-1-[((2S)-1-(4-methylphenylsulfonyl)indolin-2-yl)carbonyl]-N²-(ethyl-2-pyridine)indoline-2-carbamide TL: DM/MeOH 95:5; $R_f$ 0.19.

¹H NMR (270 MHz, (D₆) DMSO): 2.2 (s, 3H); 2.6 (m, 2H); 3.4 (m, 2H); 4.72–5.35 (m, 2H); 6.85–7.9 (m, 12H); 8.4 (m, 1H).

EXAMPLE 19

(2S)-1-[((2S)-1-(4-methylphenylsulfonyl)indolin-2-yl)carbonyl]-(4-pyridine)indoline-2-carbamide TL: DM/MeOH 95:5; $R_f$ 0.24.

¹H NMR (270 MHz, (D₆) DMSO): 2.4 (s, 3H); 3.25 (m, 2H); 4.72–5.35 (m, 2H); 6.85–8.1 (m, 16H); 8.4 (m, 1H).

EXAMPLE 20

Methyl (2R)-[4-(acetylamino)phenylsulfonyl] indoline-2-carboxylate

M.p.: 172–176° (AcOEt/PE).

TL: DM/MeOH 95:5; $R_f$ 0.44.

¹H NMR (270 MHz, (D₆) DMSO): 2.22 (s, 3H); 3.0–3.22 (m, 2H); 3.83 (s, 3H); 4.63 (dd, $J_1$=15.2, $J_2$=5.3, 1H); 6.88–7.31 (m, 4H); 7.52–7.70 (dd, $J_1$=8.9, $J_2$=8.9, 4H); 7.93 (s, 1H).

EA: cal. for $_{18}H_{18}N_2O_5S$ x ¼ H₂O (374.42): 57.74 H 4.84 N 7.48; found: 56.82 H 4.99 N 7.15.

EXAMPLE 21

(2R)-[4-(acetylamino)phenylsulfonyl]indoline-2-carboxylic acid

M.p.: 198–202°.

TL: DM/MeOH 95:5; 1% HoAc; $R_f$ 0.20.

¹H NMR (270 MHz, Dl₃): 2.08 (s, 3H); 2.97–3.34 (m, 2H); 3.78 (s, 3H); 4.86–4.92 (dd, J=15.5, 5.4, 1H); 6.95–7.36 (m, 4H); 7.67–7.78 (dd, J=9.0, 9.0, 4H); 10.33 (s, 1H); 12.97 (s, 1H).

EXAMPLE 22

Methyl (2RS)-1-({(2RS)-1-[4-(acetylamino)phenylsulfonyl]indolin-2-yl}carbonyl)indoline-2-carboxylate M.p.: 213–215° (AcOEt/PE).

TL: DM/MeOH 95:5; $R_f$ 0.31.

¹H NMR (270 MHz, DMSO): 2.07 (s, 3H); 3.02–3.46 (m, 4H); 3.76 (s, 3H); 5.18–5.69 (m, 2H); 6.95–7.40 (m, 7H); 7.71 (s, 4H); 10.33 (s, 1H).

EA: cal. for 27H₂₅N₃O₆S x 1 H₂O (537.59): 60.32 H 5.09 N 7.82; found: 60.13 H 4.89 N 7.62.

EXAMPLE 23

(2RS)-1-({(2RS)-1-[4-(acetylamino)phenylsulfonyl] indolin-2-yl}-carbonyl)indoline-2-carboxylic acid M.p.: 190–192°.

TL: DM/MeOH 95:5; $R_f$ 0.23.

¹H NMR (270 MHz, DMSO): 2.07 (s, 3H); 3.03–3.70 (m, 4H); 5.05–5.70 (m, 2H); 6.96–7.53 (m, 7H); 7.72 (4H); 7.95–8.09 (m, 1H); 10.35 (s, 1H).

EA: cal. for $_{26}H_{23}N_3O_6S$ x ½ H₂O (514.56): 60.69 H 4.70 N 8.17; found: 60.64 H 4.81 N 8.03.

The compounds of Examples 1–23 proved to be surprisingly strongly binding immunophilin modulators which are suitable and able, particularly as the carrier-immobilized form to bind pathogenic immunophilins from fluids, in particular body fluids.

The immobilized ligands were subjected to an SDS-PAGE with cell homogenate to find strongly binding Cyp B or FKBP ligands of Formula I. Carrier-immobilized ligands which have a particular affinity for the immunophilins bind these specifically with a high affinity.

The compounds of Formula I of the present invention are distinguished by immunophilin binding and inhibit its peptidyl-prolyl cis-trans isomerase (PPlase) activity. For the initial screening (1 μmol/l of substance), the inhibition of human cyclophilin B is determined in the PPlase test. This PPlase activity is determined by the aforementioned well known enzyme test.

The compounds of Formula I are preincubated at 4° C. for 15 minutes together with 10 nmol of Cyp B. The enzyme reaction is started using the test peptide Suc-Ala-Ala-Pro-Phe-Nan after addition of chymotrypsin and HEPES buffer. The change in extinction at 390 nm is then monitored and analyzed. The photometrically determined change in extinction results from two subreactions: a) the rapid chymotryptic cleavage of the trans peptide; b) the nonenzymatic cis-trans isomerization, which is catalysed by cyclophilins. The corresponding PPlase activity of the compounds of Formula I is shown in Table 1:

TABLE 1

| Compound [10 μmol] of | Inhibition [%] |
|---|---|
| Example 1 | 40 |
| Example 2 | 40 |
| Example 3 | 40 |
| Example 4 | 60 |
| Bxample 5 | 20–40 |
| Example 6 | 40 |
| Example 7 | 40 |
| Example 8 | 40–60 |
| Example 9 | 40–60 |
| Example 10 | 20–40 |
| Example 11 | 40 |
| Example 12 | 60 |
| Example 13 | 0–20 |
| Example 14 | 20 |
| Example 15 | 20 |
| Example 16 | 20–40 |
| Example 17 | 40 |
| Example 18 | 40 |
| Example 19 | 40 |
| Example 20 | 0–20 |
| Example 21 | 0–20 |
| Example 22 | 30 |
| Example 23 | 0–20 |

The formation of the supramolecule from CsA-Cyp B-calcineurin ($Ca^{2+}$-dependent phosphatase) appears to be responsible for the known immunosuppressant effects of CsA. For the investigation on the interaction with this supramolecule from CsA-Cyp B or CsA-Cyp B-calcineurin with cell homogenates of a human T-cell line, the compounds of Formula I were incubated with $^3$H-CsA (100 nmol). After gel filtration on Superose 12, the radioactivity of the eluted fractions was measured and compared with the untreated control. The corresponding displacement of $^3$H-CsA by the compounds of Formula I from the supramolecule Cyp B-CsA and Cyp-CsA-calcineurin is shown in Table 2:

TABLE 2

| Compound [10 μmol] of | Displacement from Cyp-CsA in [%] | Displacement from Cyp-CsA-CaN in [%] |
|---|---|---|
| Example 1 | 30 | −85 |
| Example 2 |  | −80 |
| Example 3 |  | −75 |
| Example 4 |  | −68 |
| Example 5 | 10 | −73 |
| Example 6 | 50 | −59 |
| Example 7 | 45 | −65 |
| Example 8 | 42 | −81 |
| Example 9 | 39 | −64 |
| Example 10 | 15 | −54 |
| Example 11 | 8 | 12 |
| Example 12 | 27 | 14 |
| Example 13 |  | 19 |
| Example 14 |  | −51 |
| Example 15 |  | −48 |
| Example 16 | 41 | −46 |
| Example 17 | 39 | −52 |
| Example 18 | 34 | −53 |
| Example 19 | 42 | −49 |
| Example 20 | 4 | 18 |
| Example 21 | 3 | 5 |
| Example 22 | 2 | 8 |
| Example 23 | 4 | 12 |

The IL-2 proliferation test is based on the incorporation of $^3$H-thymidine in T cells stimulated with OKT-3 (human anti-CD-3-antibodies) and is carried out by inoculating 100,000 T cells into microtitre plates in 150 μl of culture medium per well, stimulated by addition of OKT-3 (1 μg/ml) and incubated for 45 hours in each case with one of the compounds of Formula I. After this incubation time, 10 μl of the $^3$H-thymidine solution (0.5 μCi) are pipetted into each well. The mixture is then incubated in a 5% $CO_2$ atmosphere at 37° C. for 6 hours. After harvesting the cells, the radioactivity is quantified in a B-counter. The corresponding CD3-induced inhibition of proliferation by the compounds of Formula I is shown in Table 3.

TABLE 3

| Compound [10 μmol] of | CD3-induced inhibition of proliferation in [%] |
|---|---|
| Example 1 | 83 |
| Example 2 | 85 |
| Example 3 | 84 |
| Example 4 | 85 |
| Example 5 | 85 |
| Example 6 | 84 |
| Example 7 | 79 |
| Example 8 | 71 |
| Example 9 | 75 |
| Example 10 | 59 |
| Example 11 | 61 |
| Example 12 | 79 |
| Example 13 | 46 |
| Example 14 | 48 |
| Example 15 | 56 |
| Example 16 | 54 |
| Example 17 | 57 |
| Example 18 | 59 |
| Example 19 | 64 |
| Example 20 | 15 |
| Example 21 | 12 |
| Example 22 | 43 |
| Example 23 | 46 |

The compounds of Formula I show, like CsA, FK 506 or rapamycin, the blockade of cytokines such as TNF-α, GM-CSF, IL-2, IL-4 and IL-5, which in animal experiments cause allergically induced inflammation in the case of disease.

What is claimed is:

1. An immunophilin ligand of Formula I:

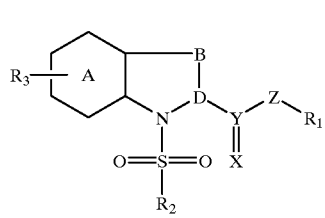

(I)

wherein

R$_1$, R$_2$ and R$_5$ are independently of each other hydrogen, C$_{1-12}$ alkyl or C$_{2-6}$ alkoxy groups in which the alkyl group is straight-chain or branched and can be substituted with a mono- or bicyclic heteroaryl residue having 1–4 heteroatoms, or mono- or polysubstituted with a phenyl ring, or R$_1$ is an amine group of an amino acid methyl ester from the group of histidine, leucine, valine, serine, threonine, pipecolic acid, 4-piperidinecarboxylic acid, 3-piperidinecarboxylic acid, —NH$_2$,-lysine, —Z-NH-lysine, -(21-Z)-NH-lysine, 2-pyridylalanine, phenylalanine, tryptophan, glutamic acid, arginine, asparagine, citrulline, homocitrulline, ornithine, thiazolecarboxylic acid, proline, 2-indolinecarboxylic acid, octahydroindolinecarboxylic acid, tetrahydroisoquinolinecarboxylic acid, 5-aminovaleric acid, and 8-aminooctanoic acid; and R$_2$ is an amino C$_{1-12}$ alkyl, or an amino C$_{2-6}$ alkoxy group wherein the alkyl group is straight-chain or branched and can be substituted with a mono- or bicyclic heteroaryl residue having 1–4 heteroatoms, or mono- or polysubstituted with a phenyl ring, R$_3$ is H, F, OR$_4$, Br, NHR$_4$, R$_4$ is hydrogen, a C$_{3-7}$ cycloalkyl, C$_{1-6}$ alkyl, or carboxy C$_{1-6}$ alkyl residue wherein the alkyl group is straight-chain or branched, A is without a ring, or an aromatic, non-aromatic, or aromatic heterocyclic or non- aromatic heterocyclic having 1–2 heteroatoms, B is CH$_2$ D is CH B-D is CH=C X is O, S, H$_2$ Y is S, C, and when X is =H$_2$ then a single bond; and Z is S, O, NR$_5$, provided that when B is CH$_2$ then D is CH, and when B is CH, then D is C, and its pharmaceutically acceptable salts.

2. The immunophilic ligand of claim 1, wherein said heteroatoms are independently of each other N, S and O.

3. The immunophilic ligand of claim 2, wherein in at least one of R$_1$, R$_2$ and R$_5$ independently of each other the alkyl group in said alkoxy group, and in R$_2$ in said amino C$_{2-6}$ alkoxy group, is substituted with a morpholine, piperazine, piperidine, pyridine, isoquinoline, quinoline, pyrimidine, oxazole, oxadiazole, isoxazole, pyrazole, pyrrole, indole, indazole, phthalazine, thiophene, furan, or imidazole group.

4. The immunophilic ligand of claim 1, wherein either of said phenyl rings in at least one of R$_1$, R$_2$ and R$_5$ is independently of each other mono- or polysubstituted with the substituent halogen, C$_{1-6}$ alkyl, C$_{3-7}$ cycloalkyl, carbamoyl, trifluoromethyl, hydroxyl, methoxy, ethoxy, benzyloxy, amino, carboxyl, or carboxyl group esterified with a straight chain or branched C$_{1-6}$ alkanol.

5. The immunophilic ligand of claim 4, wherein in at least one of R$_1$, R$_2$ and R$_5$ independently of each other said substituent is substituted with one or more of a benzyl, benzoyl, acetyl group.

6. The immunophilic ligand of claim 4, wherein in R$_2$ said substituent is substituted with a mono-, bi- or tricyclic aminoaryl or amino-heteroaryl group having 1–4 heteroatoms, or by a carboxy C$_{1-12}$ alkyl, carboxycyclopentyl, carboxycyclohexyl or benzoyl group which can be mono- or polysubstituted by a halogen, methoxy, amino, carbamoyl, trifluoromethyl, carboxyl group, or with a carboxyl residue esterified with straight-chain or branched C$_{1-6}$ alkanol.

7. The immunophilic ligand of claim 6, wherein said heteroatoms are independently of each other is N, S and O.

8. The immunophilic ligand of claim 1, wherein in R$_4$ the alkyl group in said carboxy C$_{1-6}$ alkyl group is substituted with a mono-, bi- or tricyclic carbonylaryl or carbonylheteroaryl group having 1–4 heteroatoms.

9. The immunophilic ligand of claim 8, wherein said heteroatoms are independently of each other N, S and O.

10. The immunophilic ligand of claim 8, wherein the aryl or heteroaryl group is mono- or polysubstituted with the substituent halogen, C$_{1-6}$ alkyl, C$_{3-7}$ cycloalkyl carbamoyl, trifluoromethyl, hydroxyl, methoxy, ethoxy, benzyloxy, amino, carboxyl, or carboxyl group esterified with a straight chain or branched C$_{1-6}$ alkanol.

11. The immunophilic ligand of claim 10, wherein said substituent is substituted with one or more of a benzyl, benzoyl, acetyl group.

12. An immunophilic ligand of claim 1, which comprises the compounds:

(2S)-1-[((2S)-1-(4-acetylamino)phenylsulfonyl)indolin-2-yl)carbonyl]-N-(2-methoxyethyl)indoline-2-carbamide;

(2R)-1-[((2S)-1-(4-acetylamino)phenylsulfonyl)indolin-2-yl)carbonyl]-N-(2-metboxyethyl)indoline-2-carbamide;

(2S)-1-[((2R)-1-(4-acetylamino)phenylsulfonyl)indolin-2-yl)carbonyl]-N-(2-methoxyethyl)indoline-2-carbamide;

(2R)-1-[((2R)-1-(4-acetylamino)phenylsulfonyl)indolin-2-yl)carbonyl]-N-(2-methoxyethyl)indoline-2-carbamide;

(2R,S)-1-[((2R,S)-1-(4-acetylaminophenylsulfonyl) indolin-2-yl) carbonyl]-N-(2-methoxyethyl)indoline-2-carbamide;

(2S)-1-[((2S)-1-(4-aminophenylsulfonyl)indolin-2-yl) carbonyl]-N-(2-methoxyethyl)indoline-2-carbamide;

(2S)-1-[((2S)-1-(4-aminophenylsulfonyl)prolyl) carbonyl]-N-(2-methoxy ethyl)indoline-2-carbamide;

(2S)-1-[((2S)-1-(4-aminophenylsulfonyl)pipecolyl) carbonyl]-N-(2-methoxyethyl)indoline-2-carbamide;

(2S)-1-[((2S)-1-(4-methylphenylsulfonyl)prolyl) carbonyl]-N-(2-methoxyethyl)indoline-2-carbamide;

(2S)-1-[(8-quinolinylsulfonyl)]-N-(2-methoxyethyl) indolinecarbamide;

1-[(2S)-1-(4-acetylaminophenylsulfonyl)indolin-2-yl) carbonyl]-N-leucine;

(S)-N-{(2S)-1-[4-(acetylamino)phenylsulfonyl]indolin-2-yl}carbonyl-N-(benzyloxycarbonyl)lysine methyl ester;

methyl (E)-({(2S)-1-[4-(acetylamino)phenylsulfonyl]
indolin-2-yl}carbonyl)-4-(aminophenyl)acrylate;

(2S)-1-[((2S)-1-(1-naphthalenylsulfonyl)indolin-2-yl)
carbonyl]-N-(2-methoxyethyl)indoline-2-carbamide;

(2S)-1-[((2S)-1-(2-naphthalenylsulfonyl)indolin-2-yl)
carbonyl]-N-(2-methoxyethyl)indoline-2-carbamide;

(2S)-1-[((2S)-1-(4-methylphenylsulfonyl)indolin-2-yl)
carbonyl]-N$^3$-(N-propylimidazole)indoline-2-
carbamide;

(2S)-1-[((2S)-1-(4-methylphenylsulfonyl)indolin-2-yl)
carbonyl]-N$^2$-(N-ethylmorpholine)indoline-2-
carbamide;

(2S)-1-[((2S)-1-(4-methylphenylsulfonyl)indolin-2-yl)
carbonyl]-N$^2$-(ethyl-2-pyridine)indoline-2-carbamide;

(2S)-1-[((2S)-1-(4-methylphenylsulfonyl)indolin-2-yl)
carbonyl]-(4-pyridine) indoline-2-carbamide;

methyl (2R)-[4-acetylamino)phenylsulfonyl]indoline-2-
carboxylate;

(2R)-[4-(acetylamino)phenylsulfonyl]indoline-2-
carboxylic acid;

methyl (2RS)-1-({(2RS)-1-[4-(acetylamino)
phenylsulfonyl]indolin-2-yl}carbonyl)indoline-2-
carboxylate; and (2RS)-1-({(2RS)-1-[4-(acetylamino)phenylsulfonyl]
indolin-2-yl}carbonyl) indoline-2-carboxylic acid.

13. A process for preparing a pharmacological dosage form of a drug which comprises admixing a compound of claim 1 or of claim 12 to at least one of a pharmacological carrier and excipient.

14. A pharmacological dosage form prepared by the process of claim 13, which comprises a coated or uncoated tablet, capsule, solution, ampoule, suppository, patch, or inhalable liquid or powder preparation.

15. A process for treating a patient in need therefor with a drug prepared by the process of claim 13 in a dosage form for a treatment requiring the administration of an antirheumatic, antiasthmatic, antiallergic, antipsoriatic, neuroprotectant, antiinflammatory, or immunosuppressant drug, with or without combination with another like drug.

16. The process of claim 15, wherein said immunosuppressant action is for the treatment of an immunological, autoimmune, or neurodegenerative disorder, or for the prevention of rejection reactions in transplantation, and said antiinflammatory is for the treatment of an inflammation in asthma, rhinitis, psoriasis, rheumatism, and ulcerative colitis.

17. The immunophilic ligand of claim 1, which comprises the compound in a carrier-immobilized form for binding pathogenic immunophilins from fluids, in particular body fluids.

18. A process for preparing an immunophilin ligand of claim 1, which comprises contacting a carboxylic acid derivative of Formula II (II)

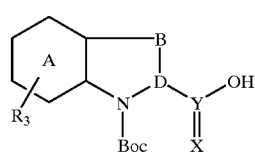

wherein $R_3$, A, B, D, X and Y are the same as in claim 1, with an amine, alkanol, halogen compound or tosylate of Formula III (III)

wherein $R_1$ and Z are the same as in claim 1, to provide an amide, ester or ether of Formula IV (IV)

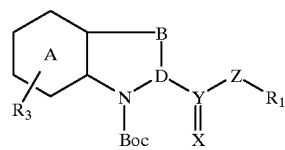

wherein $R_1$, $R_3$, A, B, D, X, Y and Z are the same as in claim 1, then contacting the compound of Formula IV with an acid to provide the compound of Formula V (V)

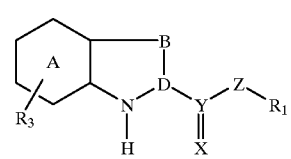

wherein $R_1$, $R_3$, A, B, D, X, Y and Z are the same as in claim 1, then contacting the compound of Formula V with a sulfochloride of Formula VI (VI)

wherein $R_2$ is the same as in claim 1, to provide the target compound of Formula I.

19. A process for preparing an immunophilin ligand of claim 1, which comprises contacting a carboxylic acid derivative of formula VII (VII)

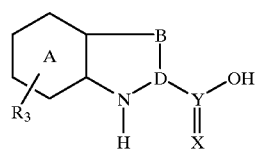

wherein $R_3$, A, B, D, X and Y are the same as in claim 1, with a sulfonyl chloride of Formula VI (VI)

wherein $R_2$ is the same as in claim 1, to provide a sulfonamide of Formula VIII

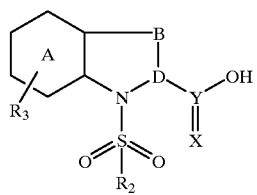
(VIII)
wherein $R_2$, $R_3$, A, B, D, X and Y are the same as in claim 1, and in a continuing reaction with a compound of Formula III
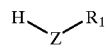
(III)
wherein $R_1$, and Z are the same as in claim 1, or with a compound of Formula V
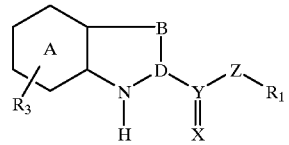
(V)
wherein $R_1$, $R_3$, X, Y, Z, A, B and D are the same as in claim 1, to provide the target compound of Formula I.
\* \* \* \* \*

UNITED STATES PATENT AND TRADEMARK OFFICE
CERTIFICATE OF CORRECTION

PATENT NO.     : 6,251,932 B1                                    Page 1 of 1
DATED          : June 26, 2001
INVENTOR(S)    : Dietmar Reichelt et al.

It is certified that error appears in the above-identified patent and that said Letters Patent is hereby corrected as shown below:

<u>Title page,</u>
Add:

-- Priority under 35 U.S.C. 120 is claimed of German Patent Application No. 19742263.2 filed on September 25, 1997 --

Signed and Sealed this

Twenty-eighth Day of May, 2002

Attest:

*Attesting Officer*

JAMES E. ROGAN
*Director of the United States Patent and Trademark Office*